United States Patent
Lee et al.

(10) Patent No.: US 11,029,305 B2
(45) Date of Patent: Jun. 8, 2021

(54) METHOD FOR EVALUATING IDENTITY OF POLYMERS AND SYSTEM USING SAME

(71) Applicant: LG Chem, Ltd., Seoul (KR)

(72) Inventors: Seung-Yup Lee, Daejeon (KR); Ji-Won Jeong, Daejeon (KR); Hye-Won Jeong, Daejeon (KR); Kyoung-Hoon Kim, Daejeon (KR)

(73) Assignee: LG Chem, Ltd.

( * ) Notice: Subject to any disclaimer, the term of this patent is extended or adjusted under 35 U.S.C. 154(b) by 1106 days.

(21) Appl. No.: 15/515,899

(22) PCT Filed: Dec. 8, 2015

(86) PCT No.: PCT/KR2015/013409
§ 371 (c)(1),
(2) Date: Mar. 30, 2017

(87) PCT Pub. No.: WO2016/099069
PCT Pub. Date: Jun. 23, 2016

(65) Prior Publication Data
US 2017/0299569 A1    Oct. 19, 2017

(30) Foreign Application Priority Data
Dec. 16, 2014  (KR) .......... 10-2014-0181513

(51) Int. Cl.
*G01N 33/44* (2006.01)
*G06F 17/11* (2006.01)
*G06F 19/00* (2018.01)

(52) U.S. Cl.
CPC ............ *G01N 33/44* (2013.01); *G06F 17/11* (2013.01); *G06F 19/00* (2013.01)

(58) Field of Classification Search
CPC .......... G01N 33/44; G06F 17/11; G06F 19/00
See application file for complete search history.

(56) References Cited

U.S. PATENT DOCUMENTS

| | | | |
|---|---|---|---|
| 5,795,782 A | 8/1998 | Church et al. | |
| 5,873,052 A | 2/1999 | Sharaf | |
| 2004/0038301 A1* | 2/2004 | Lee .................. | C08F 10/00 435/7.1 |

FOREIGN PATENT DOCUMENTS

| | | |
|---|---|---|
| JP | 3073533 B2 | 8/2000 |
| KR | 100586728 B1 | 6/2006 |
| KR | 100829706 B1 | 5/2008 |

OTHER PUBLICATIONS

International Search Report from PCT/KR2015/013409, dated Apr. 19, 2016.
Qian, et al., "Rapid Polymer Identification by In-Source Direct Pyrolysis Mass Spectrometry and Library Searching Techniques." Analytical Chemistry, vol. 68, 1996, pp. 1019-1027.

* cited by examiner

*Primary Examiner* — Manuel A Rivera Vargas
(74) *Attorney, Agent, or Firm* — Lerner, David, Littenberg, Krumholz & Mentlik, LLP

(57) ABSTRACT

This invention relates to a method of evaluating the identity of polymers and a system using the same, and more particularly to a novel method of evaluating the identity of polymers, wherein the identity of multiple polymers, rather than just one polymer, can be determined using only information about structures of the polymers, without the need to determine the characteristics of synthesized polymers through real-world experimentation. In order to evaluate the identity of polymers, the identity index PohoFactor($X_i$) for each of target polymers is developed and used, and the identity of polymers can be accurately determined on a quantitative basis by evaluating correlations between the identity indices for all polymers, the identity of which is to be determined.

10 Claims, No Drawings

METHOD FOR EVALUATING IDENTITY OF POLYMERS AND SYSTEM USING SAME

TECHNICAL FIELD

The present application is a national phase entry under 35 U.S.C. § 371 of International Application No. PCT/KR2015/013409, filed Dec. 8, 2015, published in Korean, which claims the priority from Korean Patent Application No. 10-2014-0181513, filed Dec. 16, 2014, all of which are hereby incorporated herein by reference.

The present invention relates to a method of evaluating the identity of polymers and a system using the same, and more particularly to a novel method of evaluating the identity of polymers, wherein the identity of one or more polymers may be determined using only information about structures of the polymers, without the need to determine the characteristics of synthesized polymers through real-world experimentation. In order to evaluate the identity of polymers according to the present invention, the identity index PohoFactor($X_i$) for each of target polymers is developed and used, and the identity of polymers may be accurately determined on a quantitative basis by evaluating correlations between the identity indices for all polymers, the identity of which is to be determined.

BACKGROUND ART

A polymer is configured such that a monomer is polymerized so as to be repeatedly linked, and has a high molecular weight. Since the range of characteristics of polymers can vary widely, polymers are an important class of material that is widely used in material development and product development in various fields. The factors that determine the characteristics of polymers are complicated, making it difficult to evaluate the characteristics of polymers. The characteristics of polymers vary significantly depending on the molecular weight and molecular weight distribution thereof, owing to the kind and linkage type of monomers. In order to judge whether one or more polymers exhibit identical characteristics, all target polymers are actually synthesized and the characteristics thereof are directly measured, thus evaluating whether the measurement results thereof fall within the allowable range indicating the identity. However, the synthesis of all target polymers is time-consuming and expensive. In particular, the case where the number of polymers to be determined is large is problematic because the synthesis of all polymers and then measurement of characteristics thereof are difficult in practice. However, methods of determining the identity of polymers without real-world experimentation have not yet been introduced. Hence, with the goal of efficiently developing novel materials and related products having high competitiveness by shortening the development cost and time, there is a need for a novel method able to determine the identity of polymers.

DISCLOSURE

Technical Problem

Accordingly, the present invention has been made keeping in mind the problems encountered in the art, and the present invention is intended to provide a novel method of evaluating the identity of polymers, wherein the structures of monomers as repeating units in target polymers, the identity of which is to be evaluated, are checked and produced, the identity indices PohoFactor($X_i$) of polymers are calculated, and the identity of polymers is quantitatively evaluated based on correlations between the calculated identity indices.

Technical Solution

The present invention provides a method of evaluating the identity of polymers, comprising the steps of:

a) checking structures of monomers ($X_i$) as repeating units in individual polymer structures for N polymers (N>1, a natural number), the identity of which is to be determined, and producing monomer structures, in which opposite ends thereof connected to form a polymer are substituted with a hydrogen group (—H), of the checked monomer structures;

b) calculating individual polymer identity indices PohoFactor($X_i$) for the N monomers ($X_i$) produced in step a) using Equations 1 and 2 below:

$$pohoFactor(X_i) = A \times (\alpha(X_i))^B \times \exp\left(-C \times \frac{\alpha(X_i)}{D}\right) \quad \text{[Equation 1]}$$

$$\alpha(X_i) = \frac{Surf(X_i)}{Vol(X_i)} \times \omega(X_i) \quad \text{[Equation 2]}$$

in Equations 1 and 2, $X_i$ is the $i^{th}$ monomer among N monomers produced in step a), A is a value determining the magnitude of PohoFactor, which is the polymer identity index and is a real number other than zero, B is a real number, C is a real number other than zero, D is a real number other than zero, Surf($X_i$) represents the surface area of the produced polymer structure and is an Approximate Surface Area or a Polar Surface Area, Vol($X_i$) represents the volume of the produced polymer structure and is a McGowan Molecular Volume or a Molar Volume, and $\omega(X_i)$ is one or at least one selected from the group consisting of a Partition Coefficient, a Molecular Span, a Molecular Diameter, a Molecular Eccentricity, a Molecular Asphericity, and a Molecular Radius of Gyration; and c) evaluating the correlation of the N identity indices PohoFactor($X_i$) calculated in step b), including the following steps of i) and ii): i) calculating standard deviations for N–$N_R$ identity indices obtained by sequentially excluding $N_R$ from the N identity indices, designating the $N_R$ polymer, excluded when the calculated standard deviation is minimized, to EX–SET($N_R$) and designating the standard deviation thereof to SD($N_R$), $N_R$ being a natural number from 1 to N−1, and ii) comparing the $N_R$ SD($N_R$) values calculated in step i) with a preset threshold, whereby the remaining polymers other than EX–SET($N_R$) when SD($N_R$) is less than the threshold are determined to be identical.

The threshold is a real number greater than zero.

In addition, the present invention provides a system for evaluating the identity of polymers, comprising:

a production module for checking structures of monomers ($X_i$) as repeating units in individual polymer structures for N polymers (N>1, a natural number), the identity of which is to be determined, and producing monomer structures, in which opposite ends thereof connected to form a polymer are substituted with a hydrogen group (—H), of the checked monomer structures;

a calculation module for calculating individual polymer identity indices PohoFactor($X_i$) for the N monomers ($X_i$) produced in the production module using Equations 1 and 2 below:

$$pohoFactor(X_i) = A \times (\alpha(X_i))^B \times \exp\left(-C \times \frac{\alpha(X_i)}{D}\right) \quad \text{[Equation 1]}$$

$$\alpha(X_i) = \frac{Surf(X_i)}{Vol(X_i)} \times \omega(X_i) \quad \text{[Equation 2]}$$

in Equations 1 and 2, $X_i$ is the $i^{th}$ monomer among N monomers produced in the production module, A is a value determining the magnitude of PohoFactor, which is the polymer identity index and is a real number other than zero, B is a real number, C is a real number other than zero, D is a real number other than zero, $Surf(X_i)$ represents the surface area of the produced polymer structure and is an Approximate Surface Area or a Polar Surface Area, $Vol(X_i)$ represents the volume of the produced polymer structure and is a McGowan Molecular Volume or a Molar Volume, and $\omega(X_i)$ is one or at least one selected from the group consisting of a Partition Coefficient, a Molecular Span, a Molecular Diameter, a Molecular Eccentricity, a Molecular Asphericity, and a Molecular Radius of Gyration; and an evaluation module for evaluating the correlation of the N identity indices $PohoFactor(X_i)$, calculated in the calculation module, including the following first data input module and second data input module: a first data input module for calculating standard deviations for N–$N_R$ identity indices obtained by sequentially excluding $N_R$ from the N identity indices, designating the $N_R$ polymer, excluded when the calculated standard deviation is minimized, to EX–SET($N_R$), and designating the standard deviation thereof to SD($N_R$), $N_R$ being a natural number from 1 to N–1, and a second data input module for comparing the $N_R$ SD($N_R$) values calculated in the first data input module with a preset threshold, whereby the remaining polymers other than EX–SET($N_R$) when SD($N_R$) is less than the threshold are determined to be identical.

The threshold is a real number greater than zero.

Advantageous Effects

According to the present invention, a method of evaluating the identity of polymers is able to determine the identity of one or more polymers using only information about structures of polymers, without the need to determine the characteristics of synthesized polymers through real-world experimentation. Thus, in order to determine the identity of polymers according to the present invention, individual identity indices $PohoFactor(X_i)$ for target polymers are newly defined and provided, and correlations between the identity indices for all polymers, the identity of which is to be determined, are evaluated, whereby the identity of polymers can be accurately determined on a quantitative basis. Accordingly, in the present invention, the actual synthesis of polymers is obviated, and characteristics such as the identity of polymers can be evaluated based only on the polymer structure information, thus significantly reducing the time or expense required to develop new materials and products using polymers. Hence, the present invention is expected to be very effective in terms of price competitiveness.

BEST MODE

Hereinafter, a detailed description will be given of the present invention.

For reference, constants defined in the following Equations of the present invention are values that are determined within a range in which the method of the present invention works well.

The present invention addresses a method of evaluating the identity of polymers, comprising the steps of:

a) checking structures of monomers ($X_i$) as repeating units in individual polymer structures for N polymers (N>1, a natural number), the identity of which is to be determined, and producing monomer structures, in which opposite ends thereof connected to form a polymer are substituted with a hydrogen group (—H), of the checked monomer structures;

b) calculating individual polymer identity indices $PohoFactor(X_i)$ for the N monomers ($X_i$) produced in step a) using Equations 1 and 2 below:

$$pohoFactor(X_i) = A \times (\alpha(X_i))^B \times \exp\left(-C \times \frac{\alpha(X_i)}{D}\right) \quad \text{[Equation 1]}$$

$$\alpha(X_i) = \frac{Surf(X_i)}{Vol(X_i)} \times \omega(X_i) \quad \text{[Equation 2]}$$

in Equations 1 and 2, $X_i$ is the $i^{th}$ monomer among N monomers produced in step a), A is a value determining the magnitude of PohoFactor, which is the polymer identity index and is a real number other than zero, B is a real number, C is a real number other than zero, D is a real number other than zero, $Surf(X_i)$ represents the surface area of the produced polymer structure and is an Approximate Surface Area or a Polar Surface Area, $Vol(X_i)$ represents the volume of the produced polymer structure and is a McGowan Molecular Volume or a Molar Volume, and $\omega(X_i)$ is one or at least one selected from the group consisting of a Partition Coefficient, a Molecular Span, a Molecular Diameter, a Molecular Eccentricity, a Molecular Asphericity, and a Molecular Radius of Gyration; and c) evaluating the correlation of the N identity indices $PohoFactor(X_i)$ calculated in step b), including the following steps of i) and ii): i) calculating standard deviations for N–$N_R$ identity indices obtained by sequentially excluding $N_R$ from the N identity indices, designating the $N_R$ polymer, excluded when the calculated standard deviation is minimized, to EX–SET($N_R$), and designating the standard deviation thereof to SD($N_R$), $N_R$ being a natural number from 1 to N–1, and ii) comparing the $N_R$ SD($N_R$) values calculated in step i) with a preset threshold, whereby the remaining polymers other than EX–SET($N_R$) when SD($N_R$) is less than the threshold are determined to be identical.

The threshold is a real number greater than zero.

Specifically, step a) comprises checking and producing the polymer structures for evaluating the identity of polymers, the individual structures of N polymers (N>1, a natural number), the identity of which is to be determined, are checked, and the monomer structures, as repeating units thereof, are checked. To this end, the monomer structures, in which opposite ends thereof connected to form a polymer are substituted with a hydrogen group (—H), of the checked monomer structures, are produced. In an embodiment of the present invention, as shown in Chemical Formula 1 below, when the polymer for identity evaluation is polyethylene, the repeating monomer may be determined to be $(C_2H_4)_n$ through the chemical structural formula.

In this case, the polymer is configured such that opposite ends of the monomer are repeatedly connected. The structure, the opposite ends of which are substituted with a hydrogen group (—H), is produced as shown in Chemical Formula 1 below.

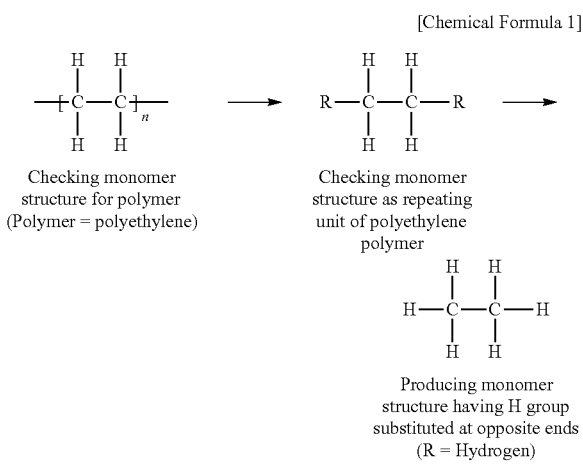

[Chemical Formula 1]

Checking monomer structure for polymer (Polymer = polyethylene)

Checking monomer structure as repeating unit of polyethylene polymer

Producing monomer structure having H group substituted at opposite ends (R = Hydrogen)

For the produced N monomers ($X_i$), the polymer identity index may be calculated in step b).

In the second step b), the polymer identity indices PohoFactor($X_i$) for the N monomers ($X_i$) produced in step a) are calculated using Equations 1 and 2 below.

$$pohoFactor(X_i) = A \times (\alpha(X_i))^B \times \exp\left(-C \times \frac{\alpha(X_i)}{D}\right) \quad \text{[Equation 1]}$$

$$\alpha(X_i) = \frac{Surf(X_i)}{Vol(X_i)} \times \omega(X_i) \quad \text{[Equation 2]}$$

In Equations 1 and 2, $X_i$ is the $i^{th}$ monomer, among N monomers produced in step a), A is a value determining the magnitude of PohoFactor, which is the polymer identity index and is a real number other than zero, B is a real number, C is a real number other than zero, D is a real number other than zero, Surf($X_i$) represents the surface area of the produced polymer structure and is an Approximate Surface Area or a Polar Surface Area, Vol($X_i$) represents the volume of the produced polymer structure and is a McGowan Molecular Volume or a Molar Volume, and $\omega(X_i)$ is one or at least one selected from the group consisting of a Partition Coefficient, a Molecular Span, a Molecular Diameter, a Molecular Eccentricity, a Molecular Asphericity, and a Molecular Radius of Gyration.

In Equation 1 of step b), it is preferred that A is a real number from 0 to 30, B is a real number from −5 to 5, C is a real number from −10 to 10, and D is a real number from 0 to 140.

In Equation 2 of step b), Surf($X_i$) represents the surface area of the polymer structure produced as described above. Although the surface area determined through various definitions by many methods may be used, the representative value may be an Approximate Surface Area or a Polar Surface Area. This value may be calculated using a variety of methods, and may be typically calculated using the ADRIANA.Code program developed by Molecular Network GmbH Computerchemie.

In Equation 2 of step b), Vol($X_i$) represents the volume of the produced polymer structure. Although the volume determined through various definitions by many methods may be used, the representative value may be a McGowan Molecular Volume or a Molar Volume. This value may be calculated using a variety of methods, and may be typically calculated using the ADRIANA.Code program developed by Molecular Network GmbH Computerchemie.

$\omega(X_i)$ represents one or at least one selected from the group consisting of a Partition Coefficient, a Molecular Span, a Molecular Diameter, a Molecular Eccentricity, a Molecular Asphericity, and a Molecular Radius of Gyration.

This value may be calculated using a variety of methods, and may be typically calculated using the ADRIANA.Code program developed by Molecular Network GmbH Computerchemie.

In the third step c), the correlation of the identity indices calculated in step b) is measured to evaluate the identity of polymers, and evaluating the correlation of N identity indices PohoFactor calculated in step b) may be performed as follows.

i) The standard deviations for the N−$N_R$ identity indices obtained by sequentially excluding $N_R$ from the N identity indices are calculated, and the $N_R$ polymer, excluded when the calculated standard deviation is minimized, is designated as EX−SET($N_R$), and the standard deviation thereof is designated as SD($N_R$). Here, $N_R$ is not particularly limited, so long as it is a natural number from 1 to N−1. For example, when $N_R$=1, the standard deviations of the N−1 identity indices resulting from excluding one value from the N identity indices are calculated. Specifically, when the first value is excluded, when the second value is excluded, . . . , when the N−$1^{th}$ value is excluded, and when the $N^{th}$ value is excluded, respective standard deviations are calculated. The one polymer, excluded when the calculated standard deviation is minimized, is designated as EX−SET(1), and the standard deviation thereof is designated as SD($N_R$).

ii) The $N_R$ SD($N_R$) values calculated in step i) are compared with the preset threshold, whereby the remaining polymers other than EX−SET($N_R$) for SD($N_R$), which is less than the threshold, are determined to be identical. Specifically, the threshold in step c) is a basis value, and is not particularly limited so long as it is a real number greater than zero. Preferably, the threshold is a real number from 0.0 to 8.0.

When the standard deviation is less than the preset threshold, the remaining polymers other than EX−SET($N_R$) are determined to be identical. More specifically, the threshold is a flexible value that may vary depending on the target polymers to be evaluated, and falls in the range of 0.0 to 8.0. As the threshold approaches zero, the tendency for the polymers to be identical is increased. The threshold is preferably set to an average of two minimum values selected from among the calculated standard deviation values SD($N_R$) after calculation of the standard deviations for the N−$N_R$ identity indices obtained by sequentially excluding $N_R$ from the N identity indices.

In addition, the present invention addresses a system for evaluating the identity of polymers using the aforementioned method of evaluating the identity of polymers.

The system for evaluating the identity of polymers according to the present invention comprises:

a production module for checking structures of monomers ($X_i$) as repeating units in individual polymer structures for N polymers (N>1, a natural number), the identity of which is to be determined, and producing monomer structures, in which opposite ends thereof connected to form a polymer are substituted with a hydrogen group (—H), of the checked monomer structures;

a calculation module for calculating individual polymer identity indices PohoFactor($X_i$) for the N monomers ($X_i$) produced in the production module using Equations 1 and 2 below:

$$pohoFactor(X_i) = A \times (\alpha(X_i))^B \times \exp\left(-C \times \frac{\alpha(X_i)}{D}\right) \quad \text{[Equation 1]}$$

$$\alpha(X_i) = \frac{Surf(X_i)}{Vol(X_i)} \times \omega(X_i) \quad \text{[Equation 2]}$$

in Equations 1 and 2, $X_i$ is the $i^{th}$ monomer among N monomers produced in the production module, A is a value determining the magnitude of PohoFactor, which is the polymer identity index and is a real number other than zero, B is a real number, C is a real number other than zero, D is a real number other than zero, $Surf(X_i)$ represents the surface area of the produced polymer structure and is an Approximate Surface Area or a Polar Surface Area, $Vol(X_i)$ represents the volume of the produced polymer structure and is a McGowan Molecular Volume or a Molar Volume, and $\omega(X_i)$ is one or at least one selected from the group consisting of a Partition Coefficient, a Molecular Span, a Molecular Diameter, a Molecular Eccentricity, a Molecular Asphericity, and a Molecular Radius of Gyration; and an evaluation module for evaluating the correlation of the N identity indices $PohoFactor(X_i)$ calculated in the calculation module, including the following first data input module and second data input module: a first data input module for calculating standard deviations for N–$N_R$ identity indices obtained by sequentially excluding $N_R$ from the N identity indices, designating the $N_R$ polymer, excluded when the calculated standard deviation is minimized, to EX–SET ($N_R$), and designating the standard deviation thereof to SD($N_R$), $N_R$ being a natural number from 1 to N–1, and a second data input module for comparing the $N_R$ SD($N_R$) values calculated in the first data input module with a preset threshold, whereby the remaining polymers other than EX–SET($N_R$) when SD($N_R$) is less than the threshold are determined to be identical.

The threshold is a real number greater than zero.

Specifically, the production module is configured such that the polymer structures for evaluating the identity of polymers are checked and produced, and individual polymer structures of the N polymers (N>1, a natural number), the identity of which is to be determined, are checked and the monomer structures as repeating units thereof are checked. To this end, monomer structures, in which the opposite ends thereof connected to form a polymer are substituted with a hydrogen group (—H), are produced, of the checked monomer structures. In an embodiment of the present invention, as shown in Chemical Formula 1 below, when the polymer for identity evaluation is polyethylene, the repeating monomer may be determined to be $(C_2H_4)_n$ through the chemical structural formula.

In this case, the polymer is configured such that opposite ends of the monomer are repeatedly connected. The structure, the opposite ends of which are substituted with a hydrogen group (—H), is produced as shown in Chemical Formula 1 below.

$$pohoFactor(X_i) = A \times (\alpha(X_i))^B \times \exp\left(-C \times \frac{\alpha(X_i)}{D}\right) \quad \text{[Equation 1]}$$

$$\alpha(X_i) = \frac{Surf(X_i)}{Vol(X_i)} \times \omega(X_i) \quad \text{[Equation 2]}$$

For the produced N monomers ($X_i$), the polymer identity index may be calculated in the calculation module.

In the calculation module as the second module, the polymer identity indices $PohoFactor(X_i)$ for the N monomers ($X_i$) produced in the production module are calculated using Equations 1 and 2 below.

[Chemical Formula 1]

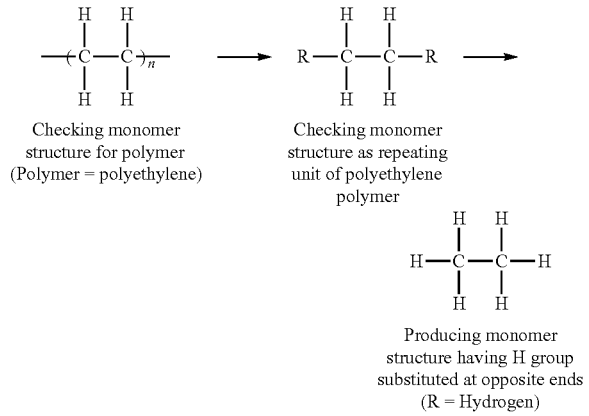

Checking monomer structure for polymer (Polymer = polyethylene)

Checking monomer structure as repeating unit of polyethylene polymer

Producing monomer structure having H group substituted at opposite ends (R = Hydrogen)

In Equations 1 and 2, $X_i$ is the $i^{th}$ monomer among N monomers produced in the production module, A is a value determining the magnitude of PohoFactor, which is the polymer identity index and is a real number other than zero, B is a real number, C is a real number other than zero, D is a real number other than zero, $Surf(X_i)$ represents the surface area of the produced polymer structure and is an Approximate Surface Area or a Polar Surface Area, $Vol(X_i)$ represents the volume of the produced polymer structure and is a McGowan Molecular Volume or a Molar Volume, and $\omega(X_i)$ is one or at least one selected from the group consisting of a Partition Coefficient, a Molecular Span, a Molecular Diameter, a Molecular Eccentricity, a Molecular Asphericity, and a Molecular Radius of Gyration.

In Equation 1 of the calculation module, it is preferred that A is a real number from 0 to 30, B is a real number from −5 to 5, C is a real number from −10 to 10, and D is a real number from 0 to 140.

In Equation 2 of the calculation module, $Surf(X_i)$ represents the surface area of the polymer structure produced as above. Although the surface area determined through various definitions by many methods may be used, the representative value may be an Approximate Surface Area or a Polar Surface Area. This value may be calculated using a variety of methods, and may be typically calculated using the ADRIANA.Code program developed by Molecular Network GmbH Computerchemie.

In Equation 2 of the calculation module, $Vol(X_i)$ represents the volume of the produced polymer structure. Although the volume determined through various definitions by many methods may be used, the representative value may be a McGowan Molecular Volume or a Molar Volume. This value may be calculated using a variety of methods, and may be typically calculated using the ADRIANA.Code program developed by Molecular Network GmbH Computerchemie.

$\omega(X_i)$ represents one or at least one selected from the group consisting of a Partition Coefficient, a Molecular Span, a Molecular Diameter, a Molecular Eccentricity, a Molecular Asphericity, and a Molecular Radius of Gyration. This value may be calculated using a variety of methods, and may be typically calculated using the ADRIANA.Code program developed by Molecular Network GmbH Computerchemie.

In the evaluation module as the third module, the correlation of the identity indices calculated in the calculation module is measured to evaluate the identity of polymers, and evaluating the correlation of N identity indices PohoFactor calculated in the calculation module may be performed using the following first and second data input modules.

The first data input module is configured such that the standard deviations for the $N-N_R$ identity indices obtained by sequentially excluding $N_R$ from the N identity indices are calculated, the $N_R$ polymer, excluded when the calculated standard deviation is minimized, is designated as EX-SET $(N_R)$, and the standard deviation thereof is designated as $SD(N_R)$. Here, $N_R$ is not particularly limited, so long as it is a natural number from 1 to N−1. For example, when $N_R=1$, the standard deviations of the N−1 identity indices resulting from excluding one value from the N identity indices are calculated. Specifically, when the first value is excluded, when the second value is excluded, . . . , when the N−1$^{th}$ value is excluded, and when the N$^{th}$ value is excluded, respective standard deviations are calculated. The one polymer, excluded when the calculated standard deviation is minimized, is designated as EX-SET(1), and the standard deviation thereof is designated as $SD(N_R)$.

The second data input module is configured such that the $N_R$ $SD(N_R)$ values calculated in the first data input module are compared with the preset threshold, whereby the remaining polymers other than EX-SET$(N_R)$ for $SD(N_R)$ less than the threshold are determined to be identical. Specifically, the threshold in the evaluation module is a basis value, and is not particularly limited so long as it is a real number greater than zero. Preferably the threshold is a real number from 0.0 to 8.0.

When the standard deviation is less than the preset threshold, the remaining polymers other than EX-SET$(N_R)$ are determined to be identical. More specifically, the threshold is a flexible value that may vary depending on the target polymers to be evaluated, and falls in the range of 0.0 to 8.0. As the threshold approaches zero, the tendency for the polymers to be identical is increased. The threshold is preferably set to an average of two minimum values selected from among the calculated standard deviation values $SD(N_R)$ after calculation of the standard deviations for the $N-N_R$ identity indices obtained by sequentially excluding $N_R$ from the N identity indices.

As used herein, the term "module" refers to a unit that is responsible for a specific function or operation, and may be embodied by hardware and software, either alone or in combination.

MODE FOR INVENTION

A better understanding of the present invention may be obtained via the following examples, which are set forth to illustrate, but are not to be construed as limiting the scope of the present invention. The scope of the present invention is given by the claims, and also contains all modifications within the meaning and range equivalent to the claims.

Example

Step 1. Checking and Production of Polymer Structure for Identity Evaluation

The following polymers (N=6) were evaluated to determine their identity. Here, Chemical Formula 2 below represents the monomer structures, in which R is substituted with hydrogen.

The structures of the monomers $(X_i)$ as the repeating units of the polymers were checked in Chemical Formula 2 below, and structures, in which R groups at opposite ends thereof connected to form the polymer were checked and completely substituted with hydrogen, were produced.

[Chemical Formula 2]

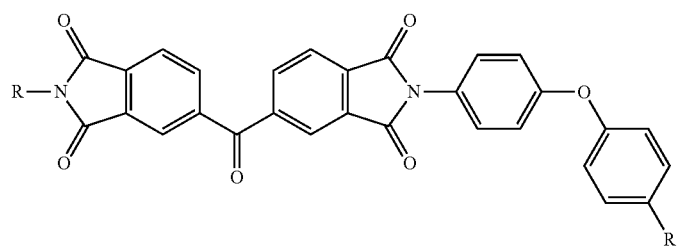

T1

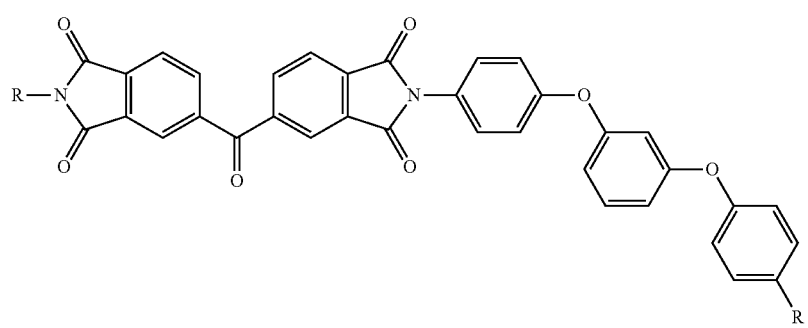

T2

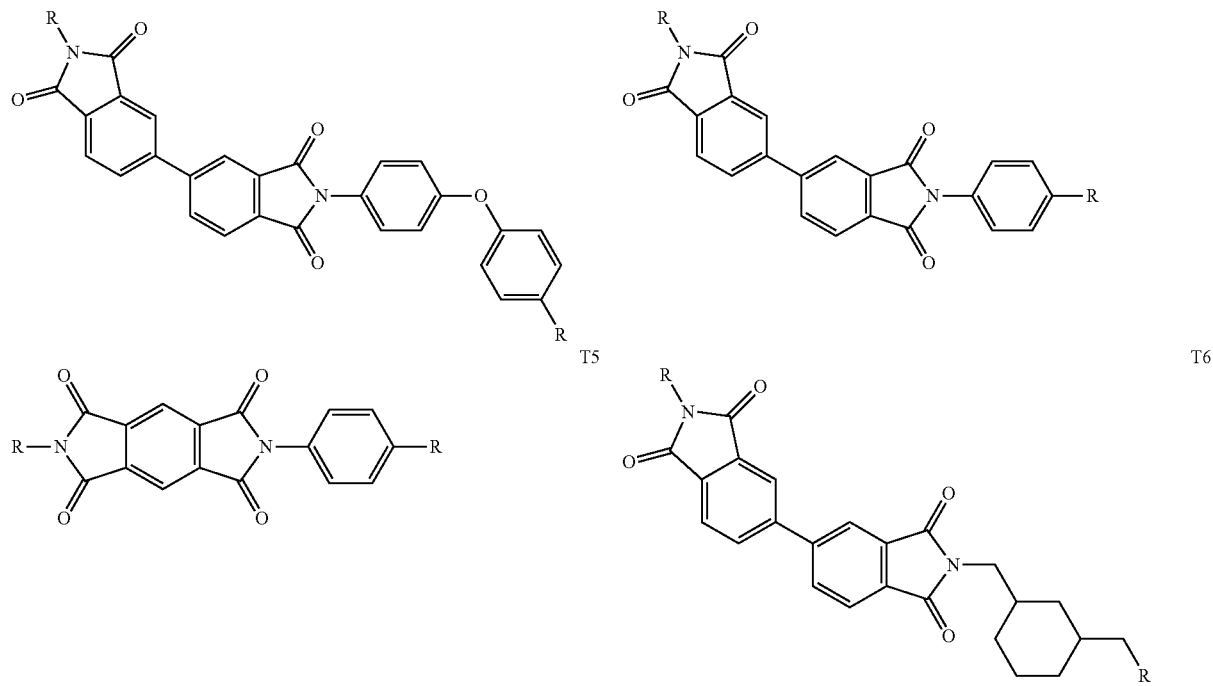

R = Hydrogen

Step 2. Calculation of Identity Index

The polymer identity indices PohoFactor($X_i$) for the monomers ($X_i$) of the six polymers produced in step 1 were calculated using Equations 1 and 2 below.

$$pohoFactor(X_i) = A \times (\alpha(X_i))^B \times \exp\left(-C \times \frac{\alpha(X_i)}{D}\right) \quad \text{[Equation 1]}$$

$$\alpha(X_i) = \frac{Surf(X_i)}{Vol(X_i)} \times \omega(X_i) \quad \text{[Equation 2]}$$

The factors designated to solve Equations 1 and 2 are shown in Table 1 below. Surf($X_i$), Vol($X_i$), and ω($X_i$) used for $X_i$, which may be calculated using various methods and programs, were calculated using the ADRIANA.Code program developed by Molecular Network GmbH Computerchemie in the present embodiment. For $X_i$=T1, T2, T3, T4, T5, and T6, respective Surf($X_1$) values were 529.2, 635.7, 498.5, 392.0, 301.9, and 480.6, respective Vol($X_1$) values were 336.4, 403.0, 320.7, 254.1, 193.3, and 295.2, and respective ω($X_i$) values were 0.989, 0.997, 0.998, 0.996, 0.991, and 0.993.

TABLE 1

| A | B | C | D | Surf | Vol | ω |
|---|---|---|---|---|---|---|
| 5.1 | 2.0 | 0.01 | 1.0 | Approximate Surface Area | McGowan Molecular Volume | Molecular Eccentricity |

PohoFactor($X_i$) values calculated for the six polymers are shown in Table 2 below.

TABLE 2

| Xi | T1 | T2 | T3 | T4 | T5 | T6 |
|---|---|---|---|---|---|---|
| PohoFactor(Xi) | 12.15 | 12.42 | 12.07 | 11.87 | 12.02 | 13.12 |

Step 3. Evaluation of Polymer Identity Through Correlation of Identity Indices $N_R$ was set to 2.

1. The case where $N_R$ is 1 was calculated. That is, standard deviations (SDs) for the identity indices obtained by sequentially excluding one value from the six identity indices are shown in Table 3 below.

TABLE 3

| | T1 | T2 | T3 | T4 | T5 | T6 | SD |
|---|---|---|---|---|---|---|---|
| 1 | X | O | O | O | O | O | 0.50 |
| 2 | O | X | O | O | O | O | 0.50 |
| 3 | O | O | X | O | O | O | 0.49 |
| 4 | O | O | O | X | O | O | 0.45 |
| 5 | O | O | O | O | X | O | 0.49 |
| 6 | O | O | O | O | O | X | 0.20 |

Table 3 shows the standard deviations when sequentially excluding one value from the six identity indices. The case excluded in the calculation of the standard deviation is represented by X, and the case included in the calculation of the standard deviation is represented by O. Specifically, in the first case, the standard deviation for the five identity indices (represented by O), remaining by excluding T1 (represented by X) from the six identity indices, is calculated to be 0.50. The standard deviations for the remaining five identity indices by sequentially excluding one value are given in Table 3.

When $N_R=1$, the case where the standard deviation is minimized was 0.20, corresponding to the case where T6 was excluded. Thus, EX-SET(1)=T6, and SD(1)=0.20.

2. The case where $N_R$ is 2 was calculated. That is, standard deviations for the identity indices resulting from sequentially excluding two values from the six identity indices are shown in Table 4 below.

TABLE 4

|    | T1 | T2 | T3 | T4 | T5 | T6 | SD   |
|----|----|----|----|----|----|----|------|
| 1  | X  | X  | ○  | ○  | ○  | ○  | 0.57 |
| 2  | X  | ○  | X  | ○  | ○  | ○  | 0.56 |
| 3  | X  | ○  | ○  | X  | ○  | ○  | 0.50 |
| 4  | X  | ○  | ○  | ○  | X  | ○  | 0.55 |
| 5  | X  | ○  | ○  | ○  | ○  | X  | 0.23 |
| 6  | ○  | X  | X  | ○  | ○  | ○  | 0.56 |
| 7  | ○  | X  | ○  | X  | ○  | ○  | 0.52 |
| 8  | ○  | X  | ○  | ○  | X  | ○  | 0.56 |
| 9  | ○  | X  | ○  | ○  | ○  | X  | 0.12 |
| 10 | ○  | ○  | X  | X  | ○  | ○  | 0.49 |
| 11 | ○  | ○  | X  | ○  | X  | ○  | 0.54 |
| 12 | ○  | ○  | X  | ○  | ○  | X  | 0.23 |
| 13 | ○  | ○  | ○  | X  | X  | ○  | 0.48 |
| 14 | ○  | ○  | ○  | X  | ○  | X  | 0.18 |
| 15 | ○  | ○  | ○  | ○  | X  | X  | 0.23 |

When $N_R=2$, the case where the standard deviation is minimized was 0.12, corresponding to the ninth case, in which T2 and T6 were excluded. As such, EX-SET(2)=T2, T6, and SD(2)=0.12.

Therefore, in an embodiment of the present invention, the threshold was set to 0.15. In this case, SD(1) was greater than the threshold, and SD(2) was smaller than the threshold. Thus, the four polymers [T1, T3, T4, T5], excluding T2 and T6, corresponding to EX-SET(2), can be determined to be identical.

In order to evaluate the identity of polymers using the above method, the identity indices PohoFactor($X_i$) for the target polymers are newly defined and represented, and the correlation between the identity indices for all polymers, the identity of which is to be determined, is evaluated, whereby the identity of polymers can be accurately determined on a quantitative basis.

The invention claimed is:

1. A method of evaluating identity of polymers, comprising steps of:
   a) checking structures of monomers ($X_i$) as repeating units in individual polymer structures for N polymers, the identity of which is to be determined, N being a natural number greater than 1, and producing monomer structures, in which opposite ends thereof connected to form a polymer are substituted with a hydrogen group (—H), of the checked monomer structures;
   b) calculating individual polymer identity indices PohoFactor($X_i$) for the N monomers ($X_i$) produced in step a) using Equations 1 and 2 below:

$$pohoFactor(X_i) = A \times (\alpha(X_i))^B \times \exp\left(-C \times \frac{\alpha(X_i)}{D}\right) \quad \text{[Equation 1]}$$

$$\alpha(X_i) = \frac{Surf(X_i)}{Vol(X_i)} \times \omega(X_i) \quad \text{[Equation 2]}$$

in Equations 1 and 2, x denotes multiplication function, and exp denotes natural exponential function, $X_i$ is an $i^{th}$ monomer among N monomers produced in step a), A is a value determining a magnitude of PohoFactor, which is the polymer identity index and is a real number other than zero, B is a real number, C is a real number other than zero, D is a real number other than zero, Surf($X_i$) represents a surface area of the produced polymer structure and is an Approximate Surface Area or a Polar Surface Area, Vol($X_i$) represents a volume of the produced polymer structure and is a McGowan Molecular Volume or a Molar Volume, and $\omega(X_i)$ is one or at least one selected from the group consisting of a Partition Coefficient, a Molecular Span, a Molecular Diameter, a Molecular Eccentricity, a Molecular Asphericity, and a Molecular Radius of Gyration; and
   c) evaluating correlation of the N identity indices PohoFactor($X_i$) calculated in step b), through the following steps of i) and ii): i) calculating standard deviations for N-$N_R$ identity indices obtained by sequentially excluding $N_R$ from the N identity indices, $N_R$ being a natural number from 1 to N-1,
   designating an $N_R$ polymer, excluded when the calculated standard deviation is minimized, to EX-SET($N_R$) and designating a standard deviation thereof to SD($N_R$), and ii) comparing the $N_R$ SD($N_R$) values calculated in step i) with a preset threshold that is a real number greater than zero, whereby the remaining polymers other than EX-SET($N_R$) when the SD($N_R$) is less than the threshold are determined to be identical.

2. The method of claim 1, wherein, in Equation 1 of step b), A is a real number from 0 to 30, B is a real number from −5 to 5, C is a real number from −10 to 10, and D is a real number from 0 to 140.

3. The method of claim 1, wherein, in Equation 2 of step b), Surf($X_i$), Vol($X_i$) and $\omega(X_i)$ are calculated using an ADRIANA.Code program.

4. The method of claim 1, wherein the threshold is set to an average of two minimum values selected from among the calculated standard deviation values SD($N_R$) after calculation of the standard deviations for the N-$N_R$ identity indices obtained by sequentially excluding $N_R$ from the N identity indices.

5. The method of claim 1, wherein the threshold is a real number from 0.0 to 8.0.

6. A system for evaluating identity of polymers, comprising:
   a production module for checking structures of monomers ($X_i$) as repeating units in individual polymer structures for N polymers, the identity of which is to be determined, N being a natural number greater than 1, and producing monomer structures, in which opposite ends thereof connected to form a polymer are substituted with a hydrogen group (—H), of the checked monomer structures;
   a calculation module for calculating individual polymer identity indices PohoFactor($X_i$) for the N monomers ($X_i$) produced in the production module using Equations 1 and 2 below:

$$pohoFactor(X_i) = A \times (\alpha(X_i))^B \times \exp\left(-C \times \frac{\alpha(X_i)}{D}\right) \quad \text{[Equation 1]}$$

$$\alpha(X_i) = \frac{Surf(X_i)}{Vol(X_i)} \times \omega(X_i) \quad \text{[Equation 2]}$$

in Equations 1 and 2, x denotes multiplication function, and exp denotes natural exponential function, $X_i$ is an $i^{th}$ monomer among N monomers produced in the production module, A is a value determining a magnitude of PohoFactor, which is the polymer identity index and is a real number other than zero, B is a real number, C is a real number other than zero, D is a real number other than zero, Surf($X_i$) represents a surface area of the produced polymer structure and is an Approximate Surface Area or a Polar Surface Area, Vol($X_i$) represents a volume of the produced polymer structure and is a McGowan Molecular Volume or a Molar Volume, and $\omega(X_i)$ is one or at least one selected from the group consisting of a Partition Coefficient, a Molecular Span, a Molecular Diameter, a Molecular Eccentricity, a Molecular Asphericity, and a Molecular Radius of Gyration; and an evaluation module for evaluating correlation of the N identity indices PohoFactor($X_i$) calculated in the calculation module, the evaluation module including a first data input module for calculating standard deviations for N–$N_R$ identity indices obtained by sequentially excluding $N_R$ from the N identity indices, $N_R$ being a natural number from 1 to N−1, designating an $N_R$ polymer, excluded when the calculated standard deviation is minimized, to EX–SET($N_R$), and designating a standard deviation thereof to SD($N_R$), and a second data input module for comparing the $N_R$ SD($N_R$) values calculated in the first data input module with a preset threshold that is a real number greater than zero, whereby the remaining polymers other than EX–SET($N_R$) when the SD($N_R$) is less than the threshold are determined to be identical.

7. The system of claim 6, wherein, in Equation 1 of the calculation module, A is a real number from 0 to 30, B is a real number from −5 to 5, C is a real number from −10 to 10, and D is a real number from 0 to 140.

8. The system of claim 6, wherein, in Equation 2 of the calculation module, Surf($X_i$), Vol($X_i$) and $\omega(X_i)$ are calculated using an ADRIANA.Code program.

9. The system of claim 6, wherein the threshold is set to an average of two minimum values selected from among the calculated standard deviation values SD($N_R$) after calculation of the standard deviations for the N–$N_R$ identity indices obtained by sequentially excluding $N_R$ from the N identity indices.

10. The system of claim 6, wherein the threshold is a real number from 0.0 to 8.0.

* * * * *